(12) United States Patent
Knoops et al.

(10) Patent No.: US 6,759,194 B1
(45) Date of Patent: Jul. 6, 2004

(54) NUCLEOTIDE SEQUENCES ENCODING PEROXISOME-ASSOCIATED POLYPEPTIDES, AND THEIR USES IN THE DIAGNOSIS AND/OR TREATMENT OF LUNG INJURIES AND DISEASES, AND OF OXIDATIVE STRESS-RELATED DISORDERS

(75) Inventors: Bernard Knoops, Cernoux-Mousty (BE); Cedric Hermans, Brussels (BE); Alfred Bernard, Brussels (BE); Ruddy Wattiez, Hyon (BE); Paul Falmagne, Mesvin (BE)

(73) Assignees: Universite Catholique de Louvain, Louvain-la Neuve (BE); Universite de Mons-Hainaut, Mons (BE)

(*) Notice: Subject to any disclaimer, the term of this patent is extended or adjusted under 35 U.S.C. 154(b) by 0 days.

(21) Appl. No.: 09/486,167

(22) PCT Filed: Aug. 20, 1998

(86) PCT No.: PCT/BE98/00124

§ 371 (c)(1),
(2), (4) Date: Aug. 15, 2000

(87) PCT Pub. No.: WO99/09054

PCT Pub. Date: Feb. 25, 1999

(30) Foreign Application Priority Data

Aug. 20, 1997 (BE) .............................. 9700692

(51) Int. Cl.[7] .......................... C12Q 1/68; C12P 21/00; C12N 1/20; C12N 15/00; C07H 21/04
(52) U.S. Cl. .................... 435/6; 435/69.1; 435/252.33; 435/320.1; 435/810; 536/23.5
(58) Field of Search ................... 435/6, 69, 1, 252.33, 435/320.1, 810; 436/23.5

(56) References Cited

U.S. PATENT DOCUMENTS 6,197,543 B1 * 3/2001 Hillman et al.

OTHER PUBLICATIONS

Hillier et al., Accession No. WO0593, Apr. 1996.*
Hiller et al., Accession No. N91311, Apr. 1996.*
Hillier et al., Accession No. W38597, May 1996.*
Hillier et al., Accession No. N64867, Mar. 1996.*
Hillier et al., Accession No. N42215, Jan. 1996.*
Hillier et al., Accession No. H20154, Jul. 1995.*
Sambrook et al., Molecular Cloning, 1989, Cold Spring Harbor Laboratory, CSH, NY, Ch. 17.*
Marra et al., Accession No. W71344, Jun. 1996.*
Attwood et al., The babel of bioinformatics, Oct. 2000, Science 290 (5491): 471–473.*
Verma et al., Nature 389:239–242, Sep. 1997.*
Das et al., BioPhar (Duluth, Minn.) 12(11): 44–46, 48, 50–51, 1999.*
Ngo et al., 1994, The Protein Folding Problem and Tertiary Structure Prediction, pp. 492–495.*
Hochstrasser et al., Putative peroxisomal antioxidant enzyme, Apr. 1993, Accession No. P30044.*
L. Hillier et al., *I64154 Hypothetical protein H10572 –Haemophilus influenzae*, Database EMBL, Accession No. N42215, Jan. 27, 1996.
Robert Strausberg, Ph.D., nq87d08.s1 NCI_*CGAP*_$C_{09}$ *Homo sapiens cDNA clone Image:1159311 similar to TR:G558080 Putative Peroxisomal Protein*, Database EMBL, Accession No. AA639384, Nov. 1, 1997.
S. Tabata, *Membrane Protein from Synechocystis SP.*, Database EMBL, Accession No. P73728, Feb. 1, 1997.

* cited by examiner

Primary Examiner—Christina Chan
Assistant Examiner—Phuong Huynh
(74) Attorney, Agent, or Firm—Knobbe, Martens, Olson & Bear, LLP (57) ABSTRACT

The present invention is related to an isolated and purified peroxisome-associated polypeptide. The present invention is also related to the nucleotide sequence encoding said amino sequence, the inhibitor directed against said sequences and their use in the diagnosis, treatment, and/or prevention of lung injuries or diseases and oxidative stress-related disorders.

4 Claims, 7 Drawing Sheets

Gene (chromosome 11q12-13)

EXONS mRNAs

Proteins

FIG. 4

CLUSTAL V alignment of human and rat B18 amino acid sequences
(Identity: 90%, Homology: 97.5%):

B18hum MAPIKVGDAIPAVEVFEGEPGNKVNLAELFKGKKGVLFGVPGAFTPGCSK = SEQIDNO1
B18rat MAPIKVGDTIPSVEVFEGEPGKKVNLAELFKDKKGVLFGVPGAFTPGCSK
       ******..*******.****.*****************

B18hum THLPGFVEQAEALKAKGVQVVACLSVNDAFVTGEWGRAHKAEGKVRLLAD
B18rat THLPGFVEQAGALKAKGAQVVACLSVNDVFVTAEWGRAHQAEGKVQLLAD
       ********.**.*****..**.**..**

B18hum PTGAFGKETDLLLDDSLVSIFGNRRLKRFSMVVQDGIVKALNVEPDGTGL
B18rat PTGAFGKETDLLLDDSLVSLFGNRRLKRFSMVIDKGVVKALNVEPDGTGL
       *****************.**********..*.*************

B18hum TCSLAPNIISQL
B18rat TCSLAPNILSQL
       ******.*

CLUSTAL V alignment of human and mouse B18 amino acid sequences
(Identity: 91%, Homology: 96%)

B18hum   MAPIKVGDAIPAVEVFEGEPGNKVNLAELFKGKKGVLFGVPGAFTPGCSK
B18mouse MAPIKVGDAIPSVEVFEGEPGKKVNLAELFKGKKGVLFGVPGAFTPGCSK
         *********.****.**************************

B18hum   THLPGFVEQAEALKAKGVQVVACLSVNDAFVTGEWGRAHKAEGKVRLLAD
B18mouse THLPGFVEQAGALKAKGAQVVACLSVNDVFVIEEWGRAHQAEGKVRLLAD
         ********.**.******.  ****.*******

B18hum   PTGAFGKETDLLLDDSLVSIFGNRRLKRFSMVVQDGIVKALNVEPDGTGL
B18mouse PTGAFGKATDLLLDDSLVSLFGNRRLKRFSMVIDNGIVKALNVEPDGTGL
         *****.*******.********...************

B18hum   TCSLAPNIISQL
B18mouse TCSLAPNILSQL
         ******.*

CLUSTAL V alignment of human and rat cDNA sequences (identity:
612/780, 78.5%):

B18hum GCCAGGAGGCGGAGTGGAAGTGGCCGTGGGGCGGGTATGGGACTAGCTGG
       ---------------TG--------CGTC--------------CTAGGCAG
                             *              ****  *

B18hum CGTGTGCGCCCTGAGACGCTCAGCGGGCTATATACTCGTCGGTGGGGCCG
B18rat CATA---GCC---GGA---TCGGTGCTCCGTGCATCGGCTACTTGGAC-
       * *    *    .  **  *  *  *  *  *   * **  *

B18hum GCGGTCAGTCTGCGGCAGCGGCAGCAAGACGGTGCAGTGAAGGAGAGTGG
B18rat -------GTGCGTGGCAGGCAGAGCAGGCCGG---AAAGGAGCAGGTTGG
              ** * ***  ** * ***   *   *      ***

FIG. 5A

```
B18hum  GCGTCTGGCGGGGTCCGCAGTTTCAGCAGAGCCGCTGCAGCCATGGCCCC
B18rat  GAGTGTGGTGGGGCCCGCAGCTTCAGCAGTGCCGCGGTGACTATGGCCCC
        * ** *** **** ****** ******** ***** *   * *******

B18hum  AATCAAGGTGGGAGATGCCATCCCAGCAGTGGAGGTGTTTGAAGGGGAGC
B18rat  GATCAAGGTGGGAGACACCATTCCCTCAGTGGAGGTATTTGAAGGGGAAC
         ************* **** **  ********** *********** *

B18hum  CAGGGAACAAGGTGAACCTGGCAGAGCTGTTCAAGGGCAAGAAGGGTGTG
B18rat  CTGGAAAGAAGGTGAACTTGGCAGAGCTGTTCAAGGACAAGAAAGGTGTT
        * ** ** ******** ***************** ****** **** ****

B18hum  CTGTTTGGAGTTCCTGGGGCCTTCACCCCTGGATGTTCCAAGACACACCT
B18rat  TTGTTTGGAGTCCCTGGGGCATTTACACCTGGCTGTTCCAAGACCCATCT
         ********** ******** ** ** ***** *********** ** **

B18hum  GCCAGGGTTTGTGGAGCAGGCTGAGGCTCTGAAGGCCAAGGGAGTCCAGG
B18rat  GCCTGGGTTTGTGGAGCAAGCCGGAGCTCTGAAGGCCAAGGGAGCACAAG
        *** **************  ** *  ****************** ** *

B18hum  TGGTGGCCTGTCTGAGTGTTAATGATGCCTTTGTGACTGGCGAGTGGGGC
B18rat  TGGTGGCCTGTCTGAGTGTTAATGATGTCTTCGTGACTGCAGAGTGGGGT
        ***************************  *** ******  *******

B18hum  CGAGCCCACAAGGCGGAAGGCAAGGTTCGGCTCCTGGCTGATCCCACTGG
B18rat  CGAGCCCACCAGGCAGAAGGCAAGGTTCAGCTCCTGGCTGACCCCACTGG
        ********* **** ************* ************ *******

B18hum  GGCCTTTGGGAAGGAGACAGACTTATTACTAGATGATTCGCTGGTGTCCA
B18rat  AGCTTTTGGAAAGGAGACAGATTTACTACTAGATGATTCTTTGGTGTCTC
         ** ***** *********** *** * *********** * ******

B18hum  TCTTTGGGAATCGACGTCTCAAGAGGTTCTCCATGGTGGTACAGGATGGC
B18rat  TCTTTGGGAATCGTCGGCTAAAAAGGTTCTCCATGGTGATAGACAAGGGC
        ************* ** ** ** *************** ** *  * ***

B18hum  ATAGTGAAGGCCCTGAATGTGGAACCAGATGGCACAGGCCTCACCTGCAG
B18rat  GTAGTAAAGGCACTGAACGTGGAGCCGGATGGCACAGGCCTCACCTGCAG
         **** ***** ***** ***** ** ***********************

B18hum  CCTGGCACCCAATATCATCTCACAGCTCTGAGGCCCTGGGCCAGATTACT
B18rat  CCTGGCCCCCAACATCCTCTCACAACTCTGAGGCCCTGA-CCAGA--ATG
        ****** ***** *** ******* ************* *****  *

B18hum  TCCTCCACCCCTCCCTATCTCACCTGCCCAGCCCTGTGCTGG-GGCCCTG
B18rat  TCCTCTGACTCTCCC-ATCTCCTCCACCCAGCTCTGGGCCAAAGGCCCAG
        *****  * ***** ***** *  ****** *** *** **  ***** *

B18hum  CA-----------------ATTGGAATG-----TTGGCCAGATTTCTGC
B18rat  TACCTCCTTACCTGAGGGCCACTGGAATGGAACCTTGACAATATTTCTGC
         *          * *******   *** * * ********

B18hum  AATAAACACTTGTGGTTTGCGGAAAAAAA--------------
B18rat  AATAAACAGTT-TAATTTGTGAAAAAAAAAAAAAAAAAAAAAAA
        ******** **   **** * ******
```

FIG. 5B

CLUSTAL V alignment of human and mouse cDNA sequences
(identity:552/675, 81.8%)

```
B18hum    GCCAGGAGGCGGAGTGGAAGTGGCCGTGGGGCGGGTATGGGACTAGCTGG
B18mouse  --------------------------------------------------

B18hum    CGTGTGCGCCCTGAGACGCTCAGCGGGCTATATACTCGTCGGTGGGGCCG
B18mouse  ----------------TGCTCCGTG----------CATCGACGTGCTTG
                          ****  *           *  ***   *    *
B18hum    GCGGTCAGTCTGCGGCAGCGGCAGCAAGACGGTGCAGTGAAGGAGAGTGG
B18mouse  GCAGGCAG--------------AGCAGGCCGG---AAAGAAGCAGGTTGG
          **  *  ***            ****  ***    *  **** **  ***
B18hum    GCGTCTGGCGGGGTCCGCAGTTTCAGCAGAGCCGCTGCAGCCATGGCCCC
B18mouse  GAGTGTGGCGGAGCCCGCAGCTTCAGCAGCTCCGCGGTGACCATGGCCCC
          *  ** ****** * ****** ******** * ****    * ********** 
B18hum    AATCAAGGTGGGAGATGCCATCCCAGCAGTGGAGGTGTTTGAAGGGGAGC
B18mouse  GATCAAGGTGGGAGATGCCATTCCCTCAGTGGAGGTATTTGAAGGGGAAC
           ******************** ***  ********** *********** *
B18hum    CAGGGAACAAGGTGAACCTGGCAGAGCTGTTCAAGGGCAAGAAGGGTGTG
B18mouse  CGGGAAAGAAGGTGAACTTGGCAGAGCTGTTCAAGGGCAAGAAAGGTGTT
          * **  ** ********  ***************************  *****
B18hum    CTGTTTGGAGTTCCTGGGGCCTTCACCCCTGGATGTTCCAAGACACACCT
B18mouse  TTGTTTGGAGTCCCTGGGGCATTTACACCTGGCTGTTCTAAGACCCACCT
           ********** ********  ** ** ***** ***** ***** ******
B18hum    GCCAGGGTTTGTGGAGCAGGCTGAGGCTCTGAAGGCCAAGGGAGTCCAGG
B18mouse  GCCTGGGTTTGTGGAGCAAGCTGGAGCTCTGAAGGCTAAGGGAGCGCAGG
          *** ************** ****  *********** ******  ****
B18hum    TGGTGGCCTGTCTGAGTGTTAATGATGCCTTTGTGACTGGCGAGTGGGGC
B18mouse  TGGTGGCCTGTCTGAGCGTTAATGACGTCTTTGTGATTGAAGAGTGGGGT
          **************** ******** * ******** **  *******
B18hum    CGAGCCCACAAGGCGGAAGGCAAGGTTCGGCTCCTGGCTGATCCCACTGG
B18mouse  CGAGCCCACCAGGCAGAAGGCAAGGTTCGGCTCCTGGCTGACCCCACTGG
          ********* **** ************************** ********
B18hum    GGCCTTTGGGAAGGAGACAGACTTATTACTAGATGATTCGCTGGTGTCCA
B18mouse  AGCCTTTGGGAAGGCGACAGACTTATTATTGGATGATTCTTTGGTGTCTC
           ************* ************* * ******* ** *******
B18hum    TCTTTGGGAATCGACGTCTCAAGAGGTTCTCCATGGTGGTACAGGATGGC
B18mouse  TCTTTGGGAATCGTCGGCTGAAAAGGTTCTCCATGGTGATAGACAACGGC
          ************* **  **  ** ************* ** *   *  ***
B18hum    ATAGTGAAGGCCCTGAATGTGGAACCAGATGGCACAGGCCTCACCTGCAG
B18mouse  ATAGTGAAGGCACTGAACGTGGAGCCAGATGGCACAGGCCTCACCTGCAG
          *********** ***** ***** **************************
B18hum    CCTGGCACCCAATATCATCTCACAGCTCTGAGGCCCTGGGCCAGATTACT
B18mouse  CCTGGCCCCCAACATCCTCTCCCAACTCTGAGGCCCTGG-CCAGATG---
          ****** ***** *** **** ** ************* ******
B18hum    TCCTCCACCCCTCCCTATCTCACCTGCCCAGCCCTGTGCTGGGGCCCTGC
B18mouse  TCCTCTGACTCTCCC-ATCTCTCCCACCCGGCTCT------AGGCC----
          *****   * ***** ***** ** *** ** **      ****
B18hum    AATTGGAATGTTGGCCAGATTTCTGCAATAAACACTTGTGGTTTGCGGAA
B18mouse  ----AAAAGGCTCGGTACCTCCTTACTGGGAGC-CACGT-----------
              *  *   * *  *  *  *    *  *    ** **
```

*FIG. 5C*

SEQUENCE LISTING

```
<160> NUMBER OF SEQ ID NOS:    4

<210> SEQ ID NO 1
<211> LENGTH: 805
<212> TYPE: DNA
<213> ORGANISM: Homo sapiens
<220> FEATURE:
<221> NAME/KEY: CDS
<222> LOCATION: (193)..(681)

<400> SEQUENCE: 1
gccaggaggc ggagtggaag tggccgtggg gcgggtatgg gactagctgg cgtgtgcgcc      60
ctgagacgct cagcgggcta tatactcgtc ggtggggccg gcggtcagtc tgcggcagcg     120
gcagcaagac ggtgcagtga aggagagtgg gcgtctggcg gggtccgcag tttcagcaga     180
gccgctgcag cc atg gcc cca atc aag gtg gga gat gcc atc cca gca gtg    231
              Met Ala Pro Ile Lys Val Gly Asp Ala Ile Pro Ala Val
                1               5                  10
```

-continued

```
gag gtg ttt gaa ggg gag cca ggg aac aag gtg aac ctg gca gag ctg     279
Glu Val Phe Glu Gly Glu Pro Gly Asn Lys Val Asn Leu Ala Glu Leu
    15                  20                  25 ttc aag ggc aag aag ggt gtg ctg ttt gga gtt cct ggg gcc ttc acc     327
Phe Lys Gly Lys Lys Gly Val Leu Phe Gly Val Pro Gly Ala Phe Thr
30                  35                  40                  45 cct gga tgt tcc aag aca cac ctg cca ggg ttt gtg gag cag gct gag     375
Pro Gly Cys Ser Lys Thr His Leu Pro Gly Phe Val Glu Gln Ala Glu
                50                  55                  60 gct ctg aag gcc aag gga gtc cag gtg gtg gcc tgt ctg agt gtt aat     423
Ala Leu Lys Ala Lys Gly Val Gln Val Val Ala Cys Leu Ser Val Asn
65                  70                  75 gat gcc ttt gtg act ggc gag tgg ggc cga gcc cac aag gcg gaa ggc     471
Asp Ala Phe Val Thr Gly Glu Trp Gly Arg Ala His Lys Ala Glu Gly
            80                  85                  90 aag gtt cgg ctc ctg gct gat ccc act ggg gcc ttt ggg aag gag aca     519
Lys Val Arg Leu Leu Ala Asp Pro Thr Gly Ala Phe Gly Lys Glu Thr
        95                  100                 105 gac tta tta cta gat gat tcg ctg gtg tcc atc ttt ggg aat cga cgt     567
Asp Leu Leu Leu Asp Asp Ser Leu Val Ser Ile Phe Gly Asn Arg Arg
110                 115                 120                 125 ctc aag agg ttc tcc atg gtg gta cag gat ggc ata gtg aag gcc ctg     615
Leu Lys Arg Phe Ser Met Val Val Gln Asp Gly Ile Val Lys Ala Leu
                130                 135                 140 aat gtg gaa cca gat ggc aca ggc ctc acc tgc agc ctg gca ccc aat     663
Asn Val Glu Pro Asp Gly Thr Gly Leu Thr Cys Ser Leu Ala Pro Asn
            145                 150                 155 atc atc tca cag ctc tga ggccctgggc cagattactt cctccacccc           711
Ile Ile Ser Gln Leu
                160 tccctatctc acctgcccag ccctgtgctg gggccctgca attggaatgt tggccagatt   771 tctgcaataa acacttgtgg tttgcggaaa aaaa                               805

<210> SEQ ID NO 2
<211> LENGTH: 162
<212> TYPE: PRT
<213> ORGANISM: Homo sapiens

<400> SEQUENCE: 2

Met Ala Pro Ile Lys Val Gly Asp Ala Ile Pro Ala Val Glu Val Phe
1               5                   10                  15

Glu Gly Glu Pro Gly Asn Lys Val Asn Leu Ala Glu Leu Phe Lys Gly
            20                  25                  30

Lys Lys Gly Val Leu Phe Gly Val Pro Gly Ala Phe Thr Pro Gly Cys
        35                  40                  45

Ser Lys Thr His Leu Pro Gly Phe Val Glu Gln Ala Glu Ala Leu Lys
    50                  55                  60

Ala Lys Gly Val Gln Val Val Ala Cys Leu Ser Val Asn Asp Ala Phe
65                  70                  75                  80

Val Thr Gly Glu Trp Gly Arg Ala His Lys Ala Glu Gly Lys Val Arg
                85                  90                  95

Leu Leu Ala Asp Pro Thr Gly Ala Phe Gly Lys Glu Thr Asp Leu Leu
            100                 105                 110

Leu Asp Asp Ser Leu Val Ser Ile Phe Gly Asn Arg Arg Leu Lys Arg
        115                 120                 125

Phe Ser Met Val Val Gln Asp Gly Ile Val Lys Ala Leu Asn Val Glu
    130                 135                 140
```

```
Pro Asp Gly Thr Gly Leu Thr Cys Ser Leu Ala Pro Asn Ile Ile Ser
145                 150                 155                 160

Gln Leu

<210> SEQ ID NO 3
<211> LENGTH: 780
<212> TYPE: DNA
<213> ORGANISM: Rattus rattus
<220> FEATURE:
<221> NAME/KEY: CDS
<222> LOCATION: (136)..(624)
<221> NAME/KEY: Unsure
<222> LOCATION: (136)..(624)
<223> OTHER INFORMATION: purine
<221> NAME/KEY: Unsure
<222> LOCATION: (323)..(323)
<223> OTHER INFORMATION: pyrimidine
<221> NAME/KEY: Unsure
<222> LOCATION: (371)..(371)
<223> OTHER INFORMATION: pyrimidine

<400> SEQUENCE: 3
tgcgtcctag gcagcatagc cggatcggtg ctccgtgcat cggctacttg gacgtgcgtg      60
gcaggcagag caggccggaa aggagcaggt tgggagtgtg gtggggcccg cagcttcagc     120
agtgccgcgg tgact atg gcc ccg atc aag gtg gga gac acc att ccc tca     171
              Met Ala Pro Ile Lys Val Gly Asp Thr Ile Pro Ser
                1               5                   10 gtg gag gta ttt gra ggg gaa cct gga aag aag gtg aac ttg gca gag     219
Val Glu Val Phe Xaa Gly Glu Pro Gly Lys Lys Val Asn Leu Ala Glu
            15                  20                  25 ctg ttc aag gac aag aaa ggt gtt ttg ttt gga gtc cct ggg gca ttt     267
Leu Phe Lys Asp Lys Lys Gly Val Leu Phe Gly Val Pro Gly Ala Phe
    30                  35                  40 aca cct ggc tgt tcc aag acc cat ctg cct ggg ttt gtg gag caa gcc     315
Thr Pro Gly Cys Ser Lys Thr His Leu Pro Gly Phe Val Glu Gln Ala
45                  50                  55                  60 gga gct cyg aag gcc aag gga gca caa gtg gtg gcc tgt ctg agt gtt     363
Gly Ala Xaa Lys Ala Lys Gly Ala Gln Val Val Ala Cys Leu Ser Val
                65                  70                  75 aat gat gyc ttc gtg act gca gag tgg ggt cga gcc cac cag gca gaa     411
Asn Asp Xaa Phe Val Thr Ala Glu Trp Gly Arg Ala His Gln Ala Glu
            80                  85                  90 ggc aag gtt cag ctc ctg gct gac ccc act gga gct ttt gga aag gag     459
Gly Lys Val Gln Leu Leu Ala Asp Pro Thr Gly Ala Phe Gly Lys Glu
    95                  100                 105 aca gat tta cta cta gat gat tct ttg gtg tct ctc ttt ggg aat cgt     507
Thr Asp Leu Leu Leu Asp Asp Ser Leu Val Ser Leu Phe Gly Asn Arg
110                 115                 120 cgg cta aaa agg ttc tcc atg gtg ata gac aag ggc gta gta aag gca     555
Arg Leu Lys Arg Phe Ser Met Val Ile Asp Lys Gly Val Val Lys Ala
125                 130                 135                 140 ctg aac gtg gag ccg gat ggc aca ggc ctc acc tgc agc ctg gcc ccc     603
Leu Asn Val Glu Pro Asp Gly Thr Gly Leu Thr Cys Ser Leu Ala Pro
                145                 150                 155 aac atc ctc tca caa ctc tga ggccctgacc agaatgtcct ctgactctcc         654
Asn Ile Leu Ser Gln Leu
                160 catctcctcc acccagctct gggccaaagg cccagtacct ccttacctga gggccactgg    714 aatggaacct tgacaatatt tctgcaataa acagtttaat ttgtgaaaaa aaaaaaaaa    774 aaaaaa                                                              780
```

```
<210> SEQ ID NO 4
<211> LENGTH: 162
<212> TYPE: PRT
<213> ORGANISM: Rattus rattus
<220> FEATURE:
<221> NAME/KEY: Modified-site
<222> LOCATION: 17
<223> OTHER INFORMATION: Glu or Gly
<221> NAME/KEY: Modified-site
<222> LOCATION: 63
<223> OTHER INFORMATION: Leu or Pro
<221> NAME/KEY: Modified-site
<222> LOCATION: 79
<223> OTHER INFORMATION: Ala or Val

<400> SEQUENCE: 4

Met Ala Pro Ile Lys Val Gly Asp Thr Ile Pro Ser Val Glu Val Phe
1               5                   10                  15

Xaa Gly Glu Pro Gly Lys Lys Val Asn Leu Ala Glu Leu Phe Lys Asp
                20                  25                  30

Lys Lys Gly Val Leu Phe Gly Val Pro Gly Ala Phe Thr Pro Gly Cys
            35                  40                  45

Ser Lys Thr His Leu Pro Gly Phe Val Glu Gln Ala Gly Ala Xaa Lys
    50                  55                  60

Ala Lys Gly Ala Gln Val Val Ala Cys Leu Ser Val Asn Asp Xaa Phe
65                  70                  75                  80

Val Thr Ala Glu Trp Gly Arg Ala His Gln Ala Glu Gly Lys Val Gln
                85                  90                  95

Leu Leu Ala Asp Pro Thr Gly Ala Phe Gly Lys Glu Thr Asp Leu Leu
            100                 105                 110

Leu Asp Asp Ser Leu Val Ser Leu Phe Gly Asn Arg Arg Leu Lys Arg
        115                 120                 125

Phe Ser Met Val Ile Asp Lys Gly Val Val Lys Ala Leu Asn Val Glu
130                 135                 140

Pro Asp Gly Thr Gly Leu Thr Cys Ser Leu Ala Pro Asn Ile Leu Ser
145                 150                 155                 160

Gln Leu
```

NUCLEOTIDE SEQUENCES ENCODING PEROXISOME-ASSOCIATED POLYPEPTIDES, AND THEIR USES IN THE DIAGNOSIS AND/OR TREATMENT OF LUNG INJURIES AND DISEASES, AND OF OXIDATIVE STRESS-RELATED DISORDERS

This U.S. National Phase application claims priority under 35 U.S.C. §371 of International Application PCT/BE98/00124, filed Aug. 20, 1998, which claims priority of Belgian application BE 9700692, filed Aug. 20, 1997.

FIELD OF THE INVENTION

The present invention is related to a new peroxisome-associated polypeptide, the nucleotide sequence encoding said polypeptide and portions thereof as well as their uses in the diagnosis of several diseases, especially the diagnosis and/or the treatment of lung injuries and diseases, and of oxidative stress-related disorders.

BACKGROUND OF THE INVENTION

The peroxisomes are organelles nearly ubiquitous in eukaryotic cells. They contain enzymes essential for various catabolic and anabolic pathways. Some of these enzymes are expressed constitutively while others can be induced under appropriate conditions. Peroxisomes carry out a variety of essential reactions such as peroxisomal oxidation and respiration, fatty acid beta-oxidation, cholesterol and dolichol metabolism, ether-phospholipid synthesis, and glyoxylate and pipecolic acid metabolism.

The peroxisomal respiratory pathway is based upon the formation of hydrogen peroxide by a collection of oxidases and the decomposition of the $H_2O_2$ by catalase These reactions are responsible for 20% of oxygen consumption in liver, and several oxidases have been identified in peroxisomes. Ethanol elimination via catalase in peroxisomes may be significant in addition to the oxidation via cytosolic alcohol dehydrogenase.

The peroxisomal beta-oxidation system catalyses the beta-oxidative chain shortening of a specific set of compounds which can not be handled by mitochondria: very long chain fatty acids, di- and trihydroxycholestanoic acids, pristanic acid, long chain dicarboxylic acids, several prostaglandins, several leukotrienes, 12- and 15-hydroxyeicosatetraeonic acid, and several mono- and polyunsaturated fatty acids, which are of direct diagnostic relevance for some peroxisomal disorders.

Peroxisomes play also a major role in the synthesis of cholesterol and other isoprenoids. Fibroblasts from patients affected by disorders of peroxisome biogenesis show low capacity to synthesise cholesterol.

Two enzyme activities responsible for introduction of the characteristic ether linkage in ether-linked phospholipids (dihydroacetonephosphate acyltransferase (DHAPAT) and alkyldihydroxyacetonephosphate synthase (alkyl-DHAP synthase)) are localised in peroxisomes. These enzymes are not yet cloned. As demonstrated by the identification of patients with deficiency of either DHAPAT or alkyl-DHAP synthase with severe clinical abnormalities, ether-phospholipids are of major importance in humans.

Peroxisomes are able to detoxify glyoxylate via alanine/glyoxylate aminotransferase. The deficiency of this cloned enzyme causes hyperoxaluria type I. L-pipecolate is a minor metabolite of L-lysine and is catabolised by the L-pipecolate oxidase localised in peroxisomes. The enzyme is deficient in cerebro-hepato-renal (Zellweger) syndrome.

In human, the importance of peroxisomes was emphasised by a number of inherited diseases involving either a defect in the biogenesis of peroxisomes or a deficiency of one (or more) peroxisomal enzymes. So far, 12 different peroxisomal disorders have been described and most of them are lethal.

A wide variety of chemicals have been showed to produce peroxisome proliferation and induction of peroxisomal and microsomal fatty acids-oxidising enzymes activities in rats and mice. Several peroxisomes proliferators have been shown to increase the incidence of liver tumours in these species. Proposed mechanisms of liver tumour formation by peroxisomes proliferators include induction of sustained oxidative stress.

Therefore, newly identified molecules associated with peroxisomes could be used for the development of diagnostic tools and possibly for the improvement of several therapeutical applications of various diseases associated with peroxisomal disorders. In addition, it is useful to identify the molecules present in specific organs like the lung and which may be used as specific markers of inflammatory diseases as well as lung injuries or diseases.

SUMMARY OF THE INVENTION

The Inventors have isolated and purified a new sequence of a low molecular weight human broncho-alveolar polypeptide. Said mammal, preferably human, protein or polypeptide (hereafter identified as B18hum protein) has been sequenced and its corresponding genomic DNA (SEQ ID NO 8) and cDNA (SEQ ID NO 1) have been identified. Similarly, the corresponding nucleotide and amino acid sequence from a rat (SEQ ID NO 3 and 4) and from a mouse (SEQ ID NO 5 and 6) have been obtained.

Said sequences present several homologies with other peroxisomal proteins of yeast and comprise a carboxy-terminal tripeptide SQL which is necessary for the specific targeting and translocation of several proteins into the peroxisome.

Therefore, the present invention is related to a new isolated and purified polypeptide sequence having a amino acid sequence which presents more than 70% homology, advantageously more than 85% homology, more preferably more than 95% homology, with the amino acid sequence SEQ ID NO 2. Said amino acid sequence is advantageously obtained from a mammal, preferably from a rat, a mouse or a human.

The present invention is also related to the isolated and purified polypeptide sequence corresponding to the amino acid sequence SEQ ID NO 2 or a portion thereof, preferably an immunoreactive portion (putative immunogenic domain or T or B cell epitopes).

Said portions are advantageously comprised between:
Glutamic acid position 14—Glutamic acid position 28
Alanine position 27—Leucine position 37
Alanine position 43—Glutamic acid position 58
Glutamic acid position 58—Valine position 70
Valine position 81—Leucine position 98
Arginine position 96—Leucine position 113
Serine position 119—Serine position 130
Valine position 138—Threonine position 151

Preferably, said portion has more than 10, 20, 30, 50 or 70 amino acids. Specific portions of the amino acid sequence SEQ ID NO 2 are also portions of more than 70 amino acids which present at least 80% of the proteinic activity (see example 5) of the complete SEQ ID NO 2 sequence. Therefore, the amino acid sequence according to the invention can be partially deleted while maintaining its activity, preferably its anti-oxidative activity, which will be described hereafter.

According to the invention, the amino acid sequence SEQ ID NO 2 presents a pI of 7.16 and a molecular weight of 17047 Dalton as hereafter defined by bidimensional electrophoresis.

The present invention is also related to the nucleotide sequence encoding the amino acid sequence according to the invention and its regulatory sequences upstream said coding sequence. A nucleotide sequence encoding the polypeptide according to the invention is a genomic DNA (see SEQ ID NO 10), a cDNA (see SEQ ID NO 1) or a mRNA, possibly comprising said upstream regulatory sequence. Advantageously, said nucleotide sequence presents more than 70%, advantageously more than 85%, more preferably more than 95% homology with SEQ ID NO 1 or its complementary strand.

According to a preferred embodiment of the present invention, said nucleotide sequence corresponds to the nucleotide sequence SEQ ID NO 1, its complementary strand or a portion thereof.

"A portion of the nucleotide sequence SEQ ID NO 1" means any nucleotide sequence of more than 15 base pairs (such as a primer, a probe or an antisense nucleotide sequence) which allow the specific identification, reconstitution or blocking of the complete nucleotide sequence SEQ ID NO 1 (including its regulatory sequences upstream the coding sequence).

Said portions allow the specific identification, reconstitution or blocking by specific hybridisation with the nucleotidic sequence SEQ ID NO 1, preferably under standard stringent conditions, with sequences like probes or primers possibly labelled with a compound (radioactive compound, enzyme, fluorescent marker, etc.), and can be used in a specific diagnostic or dosage method like probe hybridisation (see Sambrook et al., §§9.47–9.51 in *Molecular Cloning: A Laboratory Manual,* Cold Spring Harbor, Laboratory Press, Cold Spring Harbor, N.Y. (1989)), genetic amplification (like PCR (U.S. Pat. No. 4,683,195), LCR (Wu et al., *Genomics* 4, pp. 560–569), CPR (U.S. Pat. No. 5,011,769)).

Exemplary stringent hybridisation conditions are as follows: hybridisation at 42° C. in 50% formamide 5×SSC, 20 mM sodium phosphate, pH 6.8 washing in 0.2×SSC at 55° C. It is understood by those skilled in the art that variation of these conditions occur based on the length and GC nucleotide content of the sequence to be hybridised. Formulas standard in the art are appropriated for determining exact hybridisation conditions (see Sambrook et al.

Preferred examples of said nucleotide portions are as follows:

| | Sequence | Position |
|---|---|---|
| 5'-gccatcccagcagtggaggtgtttg-3' | (SEQ ID NO 11) | 217–241 |
| 5'-ttgaacagctctgccaggttcacc-3' | (SEQ ID NO 12) | 261–284 |
| 5'-tggaggtgtttgaaggggagccag-3' | (SEQ ID NO 13) | 230–253 |
| 5'-caggttcaccttgttccctggctc-3' | (SEQ ID NO 14) | 247–270 |

-continued

Figure 4:
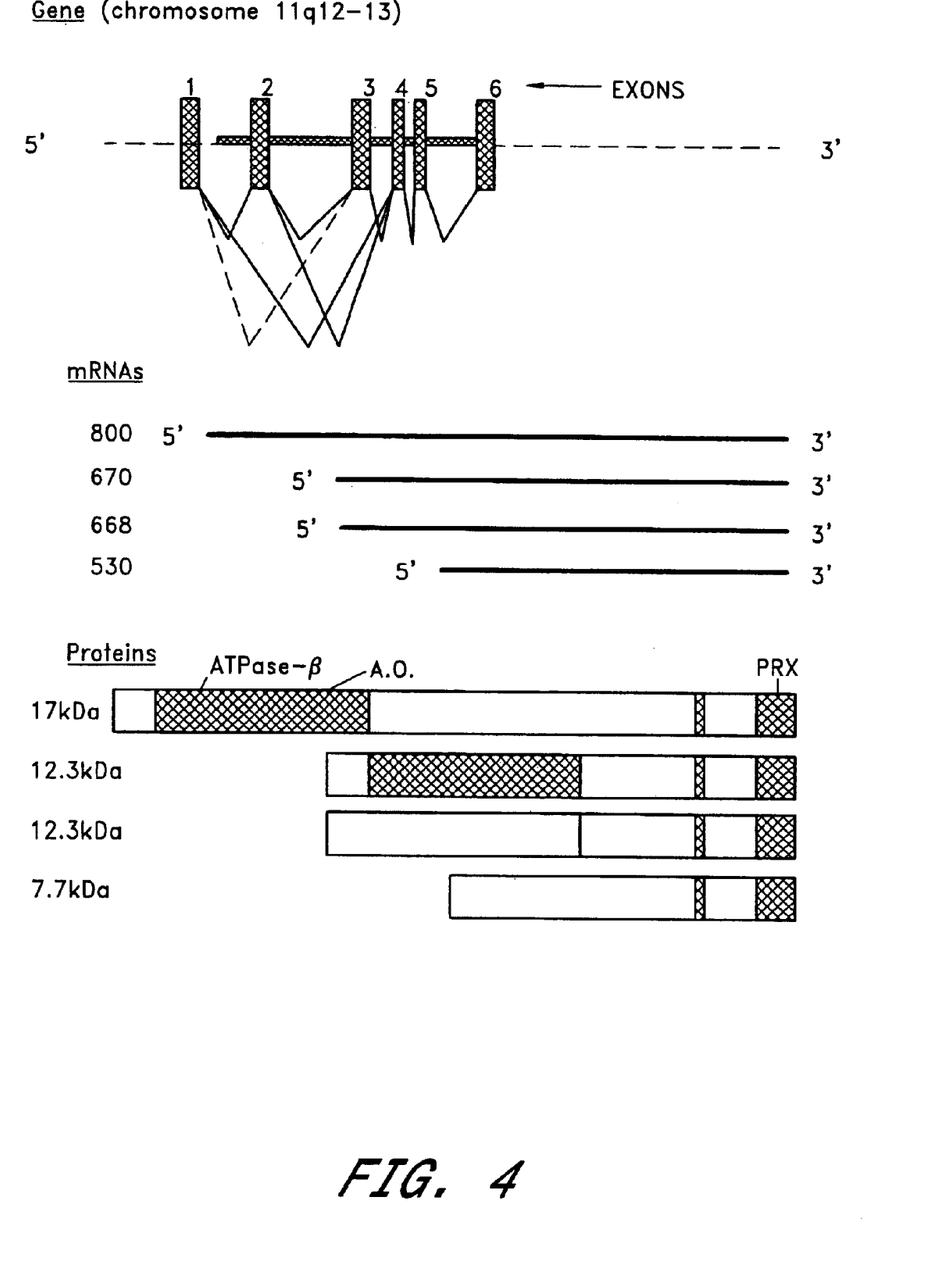
FIG. 4 is a schematic representation of the human genomic sequence, the complete cDNA sequence and the corresponding amino acid sequence.

| | Sequence | Position |
|---|---|---|
| 5'-gggtatgggactagctggcg-3' | (SEQ ID NO 15) | 33–52 |
| 5'-ctggccaacattccaattgcag-3' | (SEQ ID NO 16) | 747–768 | and the sequences of respectively 601 (SEQ ID NO 8), 604 (SEQ ID NO 9) and 469 (SEQ ID NO 7) base pairs corresponding to specific mRNA alternative splicing of the B18 human nucleotide sequence as described in FIG. 4 (the known genomic sequence incorporating several introns and exons is represented in the sequence SEQ ID NO 10).

Said sequences may be used for a genetic amplification or a probe hybridisation as above-described.

The present invention is also related to a vector comprising the necessary elements for the injection, transfection or transduction of cells and having incorporated one or more of the nucleotide sequences according to the invention. The vector according to the invention is selected from the group consisting of viruses, plasmids, phagemides, cationic vesicles, liposomes or a mixture thereof. Said vector may comprise also one or more adjacent regulatory sequences (such as promoter(s), secretion and termination signal sequence(s)), advantageously operably linked to the nucleotide sequence according to the invention.

The present invention is also related to the cell transformed by said vector and expressing the polypeptide according to the invention.

The nucleotide sequence according to the invention can be also introduced in said cell by the formation of $CaPO_4$-nucleic acid precipitate, DEAE-dextran-nucleic acid complex or by electroporation.

Another aspect of the present invention is related to an inhibitor of the polypeptide according to the invention or the nucleotide sequence according to the invention (including the upstream sequences like promoter-operator regulatory sequence which may be inhibited by a cis- and/or transactivating repressor). Said inhibitor is advantageously an antibody or a fragment of said antibody such as an hypervariable portion of said antibody directed against the amino acid or nucleotide sequence of the polypeptide according to the invention. Other examples of inhibitors according to the invention are antisense nucleotide sequences which allow the blocking of the expression of the nucleotide sequence according to the invention.

Another aspect of the present invention is related to a diagnostic device (such as a diagnostic kit or a chromatographic column) comprising an element selected from the group consisting of the amino acid sequence of said polypeptide, its nucleotide sequence, and/or the inhibitor according to the invention or a fragment thereof as above-described. Said diagnostic device may comprise also necessary reactants and media for the diagnostic and/or dosage of the nucleotide and/or amino acid sequence of the polypeptide according to the invention, which are based upon the method selected from the group consisting of in situ hybridisation, hybridisation by labelled antibodies, especially RIA (Radio Immuno Assay) or ELISA (Enzymes Linked Immuno-Sorbent Assay) technologies, detection upon filter, upon solid support, in solution, in sandwich, upon gel, dot blot hybridisation, Northern blot hybridisation, Southern blot hybridisation, isotopic or non-isotopic labelling (by immunofluorescence or biotinilised probes), genetic amplification, (especially by PCR or LCR), double immunodiffusion technique, counter-electrophoresis technique, haemagglutination or a mixture thereof.

Another aspect of the present invention concerns a diagnosis method wherein a biological sample from the patient, such as cephalo-rachidian fluid, serum, blood, plasma, urine, broncho-alveolar lavage, stomach lavage, etc., is isolated from the patient, and is put in contact with the diagnostic device according to the invention for the diagnosis or the monitoring of an injury or a disease, preferably a lung injury or an oxidative stress-related disorder, affected by the presence of pro-oxidant agent or oxidative stress such as specific cardio-vascular diseases like arteriosclerosis, neurodegenerative disorders (Alzheimer's disease, Parkinson's disease, amyotrophic lateral sclerosis), apoptosis, inflammatory reactions, allergic reactions such as asthma, hay fever and eczema, high bone mass syndrome, osteopetrosis, osteoporosis-pseudoglioma syndrome, and Bardet-Biedl syndrome 1. Said diagnosis and monitoring upon one or more biological samples obtained from several tissues from the patient can be advantageously obtained by one or more of the methods above-described, which could be adapted according to the specific biological sample by the person skilled in the art.

Figure 1:
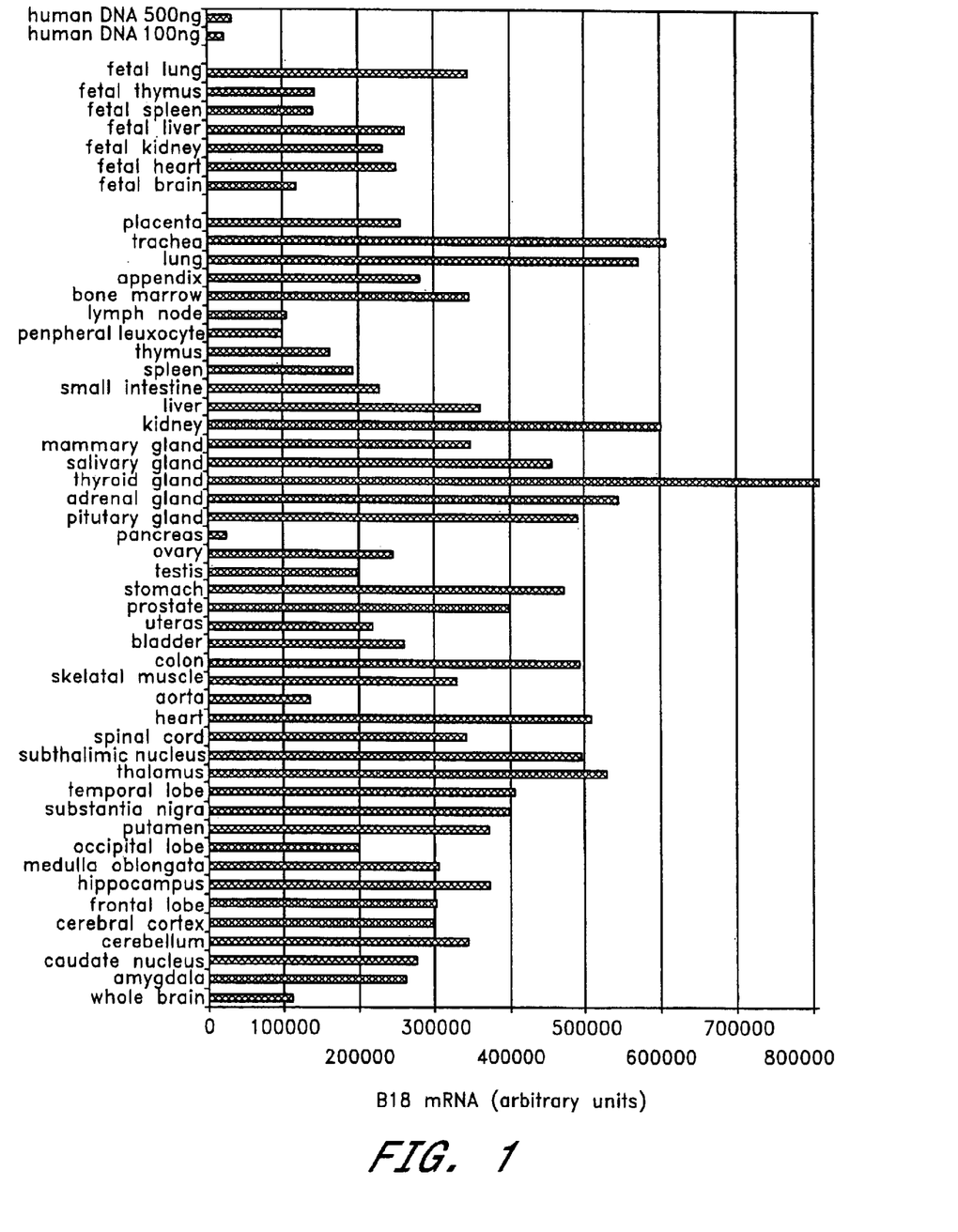
FIG. 1 represents a dot blot analysis of mRNA encoding the polypeptide according to the invention in various types of human tissues.

Therefore, the product according to the invention could be used as a marker for the above-identified injuries, diseases or disorders in a broad spectrum of tissues as shown in the enclosed FIG. 1.

A further aspect of the present invention is related to a pharmaceutical composition comprising a pharmaceutically acceptable carrier and an element selected from the group consisting of the nucleotide sequence, the amino acid sequence of the polypeptide according to the invention, the inhibitor directed against said sequences and/or one or more portions thereof.

A last aspect of the present invention is related to the use of the pharmaceutical composition according to the invention for the manufacture of a medicament in the treatment and/or the prevention of lung injuries and/or diseases or of oxidative stress-related disorders.

The present invention is also related to a prevention and/or treatment method of a patient, especially a human patient, preferably affected by lung injuries and/or diseases or by oxidative stress-related disorders, wherein a sufficient amount of the pharmaceutical composition according to the invention is administered to said patient in order to treat, avoid and/or reduce the symptoms of said injuries and/or diseases.

Other injuries and/or diseases which can be prevented and/or treated are injuries and/or diseases affected by the presence of pro-oxidant agents or oxidative stress, such as specific cardio-vascular diseases like arteriosclerosis, neurodegenerative disorders such as Alzheimer's disease, Parkinson's disease, amyotrophic lateral sclerosis, apoptosis and inflammatory reactions and some allergic reactions such as asthma, hay fever and eczema, high bone mass syndrome, osteopetrosis, osteoporosis-pseudoglioma syndrome, and Bardet-Biedl syndrome 1.

The pharmaceutically acceptable carrier according to the invention is any compatible non-toxic substance suitable for administering the composition according to the invention to a human patient. Pharmaceutically acceptable carriers according to the invention suitable for oral administration are the ones well known by the person. skilled in the art, such as tablets, coated or non-coated pills, capsules, spray-gas, patches, gels, solutions or syrups. Pharmaceutically acceptable carriers vary according to the mode of administration (intravenous, intramuscular, subcutaneous, parenteral, etc.), and may comprise also adjuvants well known by the person skilled in the art to increase, reduce and/or regulate humoral, local and/or cellular response of the immune system.

The pharmaceutical composition according to the invention may be prepared by the methods, generally applied by the person skilled in the art in the preparation of various pharmaceutical compositions, wherein the percentage of the active compound/pharmaceutically acceptable carrier can vary within very large ranges, only limited by the tolerance of the patient to said pharmaceutical composition, and wherein the limits are particularly determined by the frequency of administration and the possible side-effects of the active compounds or its pharmaceutically acceptable carrier.

Another aspect of the invention is related to the use of the diagnostic device according to the invention for performing upon the patient or upon a biological fluid obtained from the patient, a diagnosis, a dosage and/or a monitoring of the above-mentioned injuries or diseases or oxidative stress-related disorders affecting the patient.

A further aspect of the present invention is related to a cell or a non-human animal, preferably a mammal such as a mouse or a rat, transformed by the vector according to the invention and overexpressing the polypeptide according to the invention, or a non-human animal, preferably a mammal such as a mouse or a rat, genetically modified by a partial or total deletion of its genomic sequence encoding the polypeptide according to the invention (knock-out non-human mammal) and obtained by methods well known by the person skilled in the art such as the one described by Kahn et al. (*Cell*, Vol. 92, pp. 593–596 (March 1998)).

Other examples of genetically modified non-human animals according to the invention may be a transgenic non-human animal comprising an inhibitor according to the invention, preferably an antisense nucleic acid sequence complementary to the nucleotide sequence according to the invention so placed as to be transcribed into antisense MRNA which is complementary to the nucleotide sequence according to the invention and which hybridises to said nucleotide sequence, thereby reducing or blocking its translation.

Further aspects of the present invention will be described in the enclosed non-limiting examples in reference to the following Figures.

BRIEF DESCRIPTION OF THE DRAWINGS

FIG. 5A–C represents respectively the alignment of the sequences of the human B18 polypeptide according to the invention (SEQ ID NO: 2) with the corresponding rat (SEQ ID NO: 4) and mouse (SEQ ID NO: 6) sequences.

EXAMPLE 1

Homology Between the B18 Polypeptide According to the Invention with Other Known Nucleotide or Amino Acid Sequences The BLAST 2.0 software (gapped BLAST at the NCBI Internet site) was used for searching for homologies between human B18 (162 amino acids) and known polypeptides in databases (GenBank, SwissProt). Said search did not give perfect alignment with known peptides from different species (Table 1). Homologies of the human B18 cDNA (805 nucleotides) with GenBank, EMBL, DDBJ and PDB deposited nucleotide sequences (Table 2) and GenBank Expression Sequence TAGS (ESTs) were noted.

TABLE 1

Homologies of the B18 proteins (162 amino acid) with other proteins

| Name | NCBI ID | Identity (%) Homology (%) |
|---|---|---|
| Membrane protein (*synechocystis* sp.) | 1652859 | 57/129 (44%) 81/129 (62%) |
| Peroxisomal-like protein (*Aspergillus fumigatus*) | 2769700 | 56/176 (31%) 90/176 (50%) |
| Haein HI0572 hypothetical protein (*Haemophilus influenzae*) | 1723174 | 53/146 (36%) 80/146 (54%) |
| PMP20 (*Schizosaccharomyces pombe*) | AJ002536 | 54/161 (33%) 85/161 (52%) |
| Peroxisomal membrane protein A (PMP 20) (*Candida boidinii*) | 130360 | 59/170 (34%) 89/170 (51%) |
| Peroxisomal membrane protein B (PMP 20) (*Candida boidinii*) | 130361 | 58/170 (34%) 88/170 (51%) |
| Putative peroxisomal protein PMP from yeast (*Saccharomyces cerevisiae*) | 1709682 | 41/138 (29%) 72/136 (51%) |
| Alkylhydroperoxide reductase C22 protein (*Escherichia coli*) | P26427 | 36/126 (28%) 56/126 (45%) |

TABLE 2

| Name | Access NO | Identity |
|---|---|---|
| Human mRNA down-regulated in cells infected by adenovirus 5 | U82616 | 259/263 (98%) |
| Human mRNA down-regulated in cells infected by adenovirus 5 | U82615 | 300/321 (93%) |

In the Table 2, an identity of 98% has been obtained with the alignment of 259 nucleotides of CDNA B18, which comprises in its totality 805 nucleotides, with 263 nucleotides of U82616 CDNA. A similar identity has been obtained with the U82615 sequence.

The sequence SEQ ID NO 1 comprising 805 nucleotides presents a homology with several EST sequences obtained from a human and from a mouse, having the following references:
Human
  AA130751, N42215, W38597, N91311, N68467, AA187737, N68916, W00593, R88950, AA181884, H20154, H66666
Mouse
  AA220019, AA123351, AA087129, AA255021, AA249897, W71344

EXAMPLE 2

Tissue Detection

A human RNA master Blot (Clontech) containing 100–500 ng of poly-A+human RNA in each dot (normalised to the mRNA expression levels of eight different housekeeping genes) was hybridised with a 554 bp-long B18 probe labelled with $^{32}$P, and quantified using Phosphorimaging Technology. As shown in FIG. 1, B18 mRNA is present in all tissues examined but predominantly in trachea, lung, kidney, thyroid gland, stomach, colon, heart and some regions of the brain. Highest expression has been noted in the thyroid tissue. This presence is probably correlated with the possible antioxidant activity of the B18 polypeptide according to the invention.

EXAMPLE 3

Inflammatory Reaction

Figure 2:
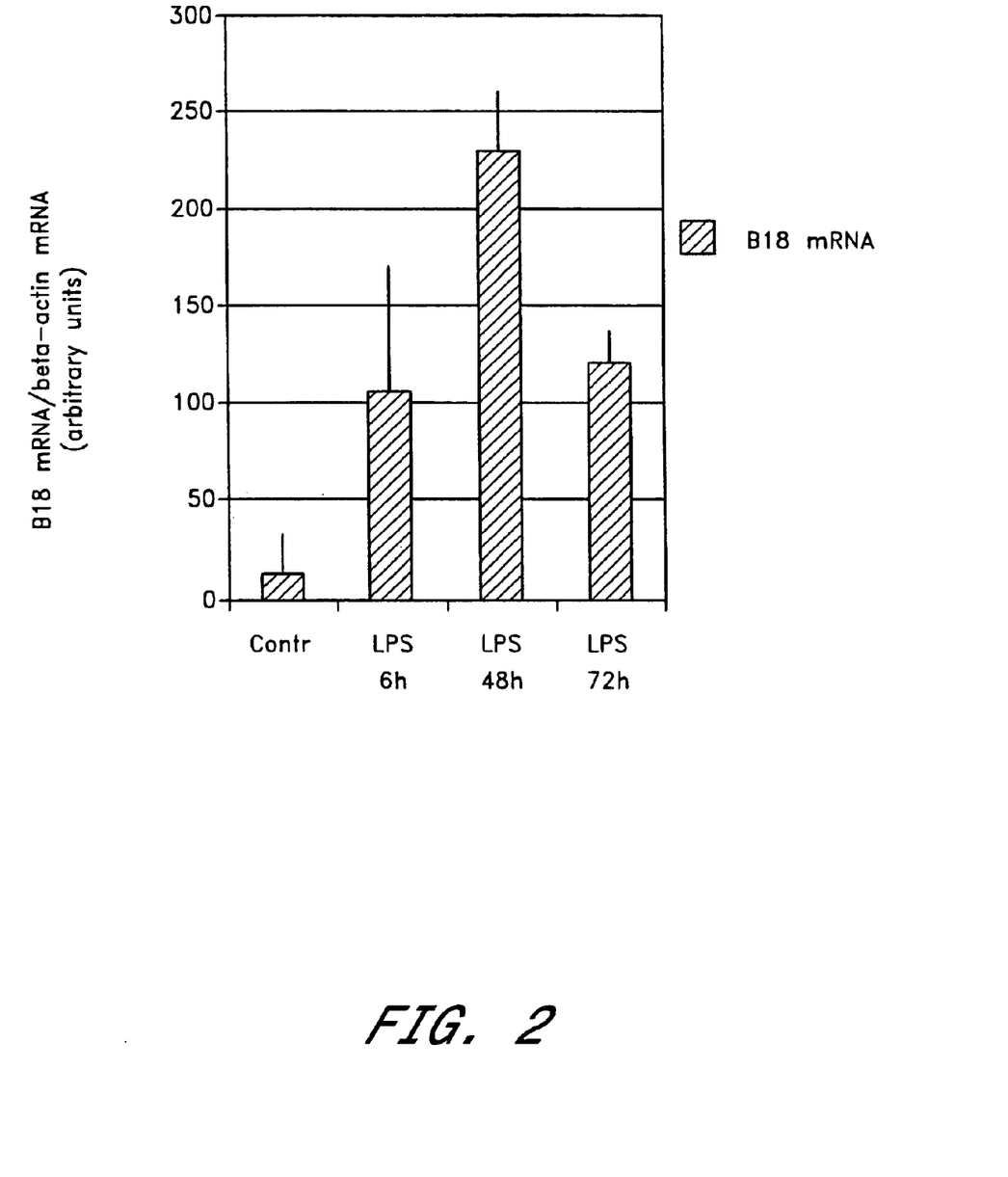
FIG. 2 represents a Northern blot analysis of mRNA encoding the polypeptide according to the invention in a rat lung after administration of lipopolysaccharides (LPS) inducing an inflammatory reaction of the lung.

FIG. 2 represents a Northern blot analysis of rat lung mRNA after 6, 48 and 72 hours after lipopolysaccharides (LPS) instillation inducing an inflammatory reaction in the lung.

A Northern blot containing 15 µg of total RNA in each lane was hybridised with a 225 bp-long rat B18 probe, stripped and reprobed with a 572 bp-long rat β-actin probe, both labelled with $^{32}$P. Northern blot was quantified using Phosphorimaging Technology and the B18 mRNA data were normalised to β-actin mRNA level.

EXAMPLE 4

Pneumotoxic Reaction

Figure 3:
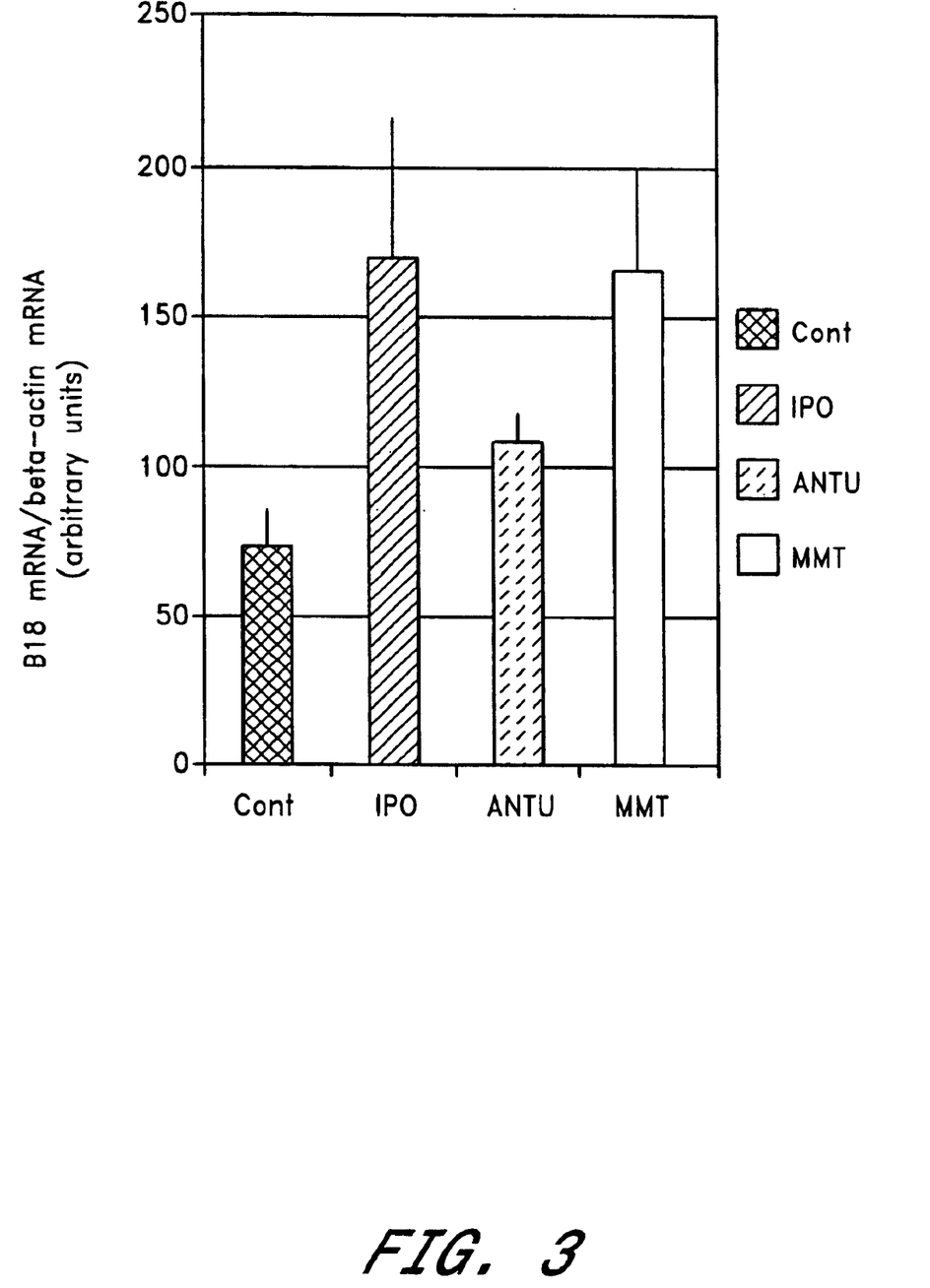
FIG. 3 represents a Northern blot analysis of mRNA encoding the polypeptide according to the invention in a rat lung after intraperitoneal injection of pneumotoxicants.

FIG. 3 represents a Northern blot analysis of rat lung mRNA after intraperitoneal injection of pneumotoxicants (4-ipomeanol, 1-(3-fyryl)-4-hydroxypentanone (IPO), methylcyclopentadienyl manganese tricarbonyl (MMT) or alpha naphtylthiourea (ANTU)). These agents are known to induce in the lung acute lesions of Clara (IPO) and alveolar cells (MMT) as well as increasing the permeability of the alveolar/blood barrier (ANTU). A Northern blot containing 15 µg of total RNA in each lane was hybridised with a 225 bp-long rat B18 probe, stripped and reprobed with a 572 bp-long β-actin probe both labelled with $^{32}$P. The Northern blot was quantified using Phosphorimaging Technology and rat B18 mRNA data were normalised to β-actin mRNA level.

EXAMPLE 5

Proteinic Activity of the B18 Polypeptide

An amino analysis of the complete human B18 amino acid sequence shows that said polypeptide presents specific portions showing a homology with other antioxidant enzymes (starting from a Leucine at position 37 until a Cysteine at position 48) and another portion having an important homology with beta chains of ATP synthase (starting from a Glutamic acid at position 14 until a Glycine in position 39).

Furthermore, the B18 amino acid sequence according to the invention shows an important homology with an *Aspergillus fumigatus* allergen (34% identity and 60% homology by using clustal V sequence alignment), especially upon the portion of said B18 polypeptide having possible antioxidant properties. Therefore, it is possible that a peroxisomal protein (possibly homologous to B18 protein) is able to induce and to bind IgE from patients sensitised to *Aspergillus fumigatus* peroxisomal proteins after an induction of the patient immune system with *Aspergillus fumigatus* allergen. This mechanism can be compared to a reaction obtained with the manganese superoxide dismutase (MnSOD) wherein the human MnSOD is able to bind to IgE from patients sensitised to *Aspergillus fumigatus* MnSOD.

Furthermore, the Inventors have identified a position of the B18 polypeptide which presents a homology with a Cyclophilin-binding domain of *Candida boidinii* PMP20 (receptor of the immuno-suppresant drug cyclosporine A). Said possible Cyclophilin-binding domain is starting from the Threonine in position 151 until the Leucine in position 162.

EXAMPLE 6:

B18 Human Gene and mRNA Alternative Splicing

As represented in the enclosed FIG. 4, the Inventors have identified upon the genomic DNA (SEQ ID NO: 10) 5 exons and 5 introns. By RT-PCR (using primers 5'-gggtatgggactagctggcg-3' (SEQ ID NO: 15) and 5'-ctggccaacattccaattgcag-3'(SEQ ID NO: 16)) and according to the genomic sequence, 4 different cDNAs corresponding to the transcription of the said genomic DNA have been identified in human lung and in human brain. A first cDNA of 736 bp corresponds to the cDNA encoding the complete amino acid sequence of the B18 protein according to the invention. However, 3 other cDNAs of 601, 604, and 469 bp were also identified, and comprise specific splicings of one of more exons.

Therefore, another aspect of the present invention is related to said specific portions of the complete genomic or CDNA nucleotide sequence according to the invention or to specific portions of the complete amino acid sequence of the B18 protein according to the invention, which could be used also as specific markers of the B18 activity, preferably the anti-oxidative activity.

EXAMPLE 7

Knock-out Mouse

Exons of a mouse genomic sequence encoding the B18 polypeptide according to the invention have been deleted by homologous recombination. Said homologous recombination has been obtained with a genetic sequence comprising a neomycin resistant gene. The targeting vector with said gene and a thymidine kinase (in order to eliminate non-homologous recombinants with ganciclovir) has been prepared. Said recombination was used for the deletion of one or more exons of the B18 polypeptide. After electroporation of ES cells with the targeting vector, positive clones having incorporated homologous recombination were identified by Southern blot with labelled probes. Aggregation of said positive clones with a morula from a Swiss pseudo-pregnant mouse produces several chimeric mice which survive after birth. Several homozygote mice are obtained by cross-breeding and are used as a model for the above-mentioned diseases.

Figure 5B:
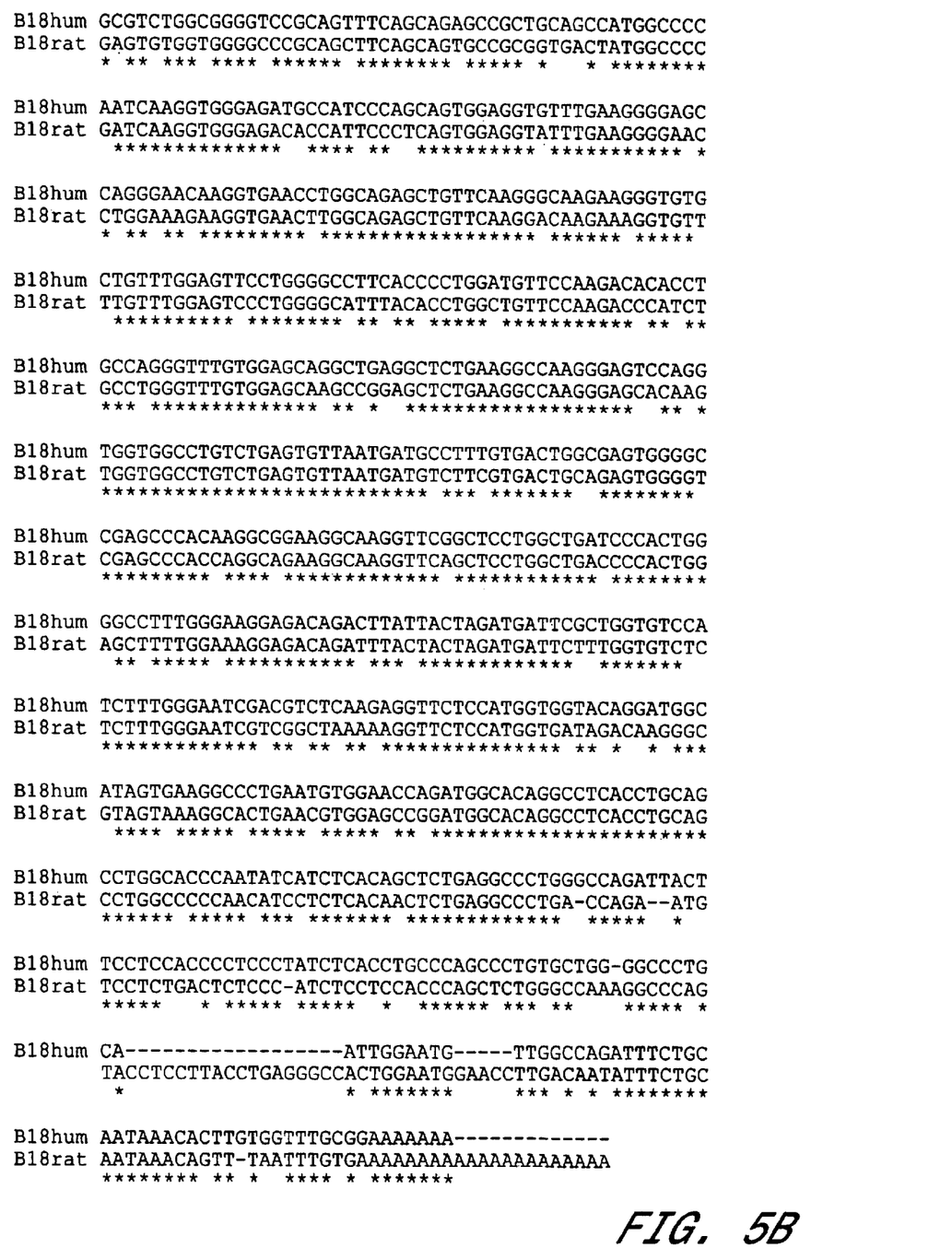

Similar experiments may be done with another mammal whose B18 sequence is known (the B18 sequence of a mouse and a rat and their alignment with the human sequence is shown in the enclosed FIG. 5).

EXAMPLE 8

Chromosome Localisition of Human B18 Gene

Radiation hybrid clones (GeneBridge 4 Radiation Hybrid Panel, Research Genetics) were used for performing chromosome localisation by PCR with two different pairs of primers (5'-caggttcaccttgttccctggctc-3' (SEQ ID NO 14), 5'-atgttatgcaaccctttgcgacac-3' (SEQ ID NO 17) and 5'-gtgtttgaaggggagccagggaac-3' (SEQ ID NO 18), 5'-agagacagggtttcaccatcttgg-3' (SEQ ID NO 19)).

The Inventors have located B18 genomic sequence on human chromosome 11q13. B18 gene has been located 7.15-6.1 cR from marker D11S913 between markers D11S1963 and D11S4407 (Genome Database internet site).

Unknown genes linked to different disorders have been localised in the same region of chromosome 11. Therefore, B18 gene is possibly associated with these disorders:

atopy (atopic hypersensitivity: asthma, hay fever and eczema; MIM °No. 147050 at OMIM of NCBI internet site), high bone mass syndrome (MIM °No. 601884), osteoporosis (MIM °No. 259700), osteoporosis-pseudoglioma syndrome (MIM °No.601884) and Bardet-Biedl syndrome 1(MIM °No. 209901).

What is claimed is:

1. An isolated or purified polynucleotide consisting of SEQ ID NO: 1 or its complementary strand.
2. A vector comprising the polynucleotide of claim 1.
3. A diagnostic device comprising the polynucleotide of claim 1.
4. An isolated cell transformed by the vector according to claim 2.

* * * * *